United States Patent [19]

Green et al.

[11] Patent Number: 5,235,070

[45] Date of Patent: * Aug. 10, 1993

[54] SUPPRESSION OF DUST FROM SOLID AROMATIC ANHYDRIDES

[75] Inventors: Michael R. Green, Geneva; Chang M. Park; Adel B. Abdul-Malek, both of Naperville, all of Ill.

[73] Assignee: Amoco Corporation, Chicago, Ill.

[*] Notice: The portion of the term of this patent subsequent to Aug. 7, 2007 has been disclaimed.

[21] Appl. No.: 732,648

[22] Filed: Jul. 19, 1991

Related U.S. Application Data

[63] Continuation of Ser. No. 605,519, Oct. 29, 1990, abandoned, which is a continuation of Ser. No. 423,373, Oct. 19, 1989, abandoned, which is a continuation-in-part of Ser. No. 279,430, Dec. 2, 1988, Pat. No. 4,946,970.

[51] Int. Cl.[5] ........................................... C07D 277/22
[52] U.S. Cl. .................................... 549/203; 549/239; 549/241; 549/242; 549/245; 549/247; 549/249; 549/250
[58] Field of Search ............... 549/239, 241, 242, 245, 549/247, 249, 250, 203

[56] References Cited

U.S. PATENT DOCUMENTS

| | | | |
|---|---|---|---|
| 3,915,637 | 10/1975 | Taylor | 23/230 B |
| 4,208,433 | 6/1980 | Barham, Jr. et al. | 426/69 |
| 4,490,511 | 12/1984 | Li et al. | 525/507 |

FOREIGN PATENT DOCUMENTS

| | | |
|---|---|---|
| 919031 | 1/1973 | Canada . |
| 0292131 | 11/1988 | European Pat. Off. . |
| 0950559 | 10/1956 | Fed. Rep. of Germany . |
| 2538276 | 4/1977 | Fed. Rep. of Germany . |

OTHER PUBLICATIONS

JP abstract 80037521 (1980).
JP abstract 56059701 (1981).

*Primary Examiner*—Thurman K. Page
*Assistant Examiner*—Jyothsna Venkas
*Attorney, Agent, or Firm*—Thomas E. Nemo; Wallace L. Oliver; Frank J. Sroka

[57] ABSTRACT

A method for reducing the formation of dust produced by solid aromatic anhydrides, and aromatic anhydride compositions that have a reduced tendency to emit aromatic anhydride dust, are disclosed. The method comprises treating the aromatic anhydride with low levels of suitable organic compounds.

18 Claims, No Drawings

SUPPRESSION OF DUST FROM SOLID AROMATIC ANHYDRIDES

This is a continuation of application Ser. No.07/605,519, filed Oct. 29, 1990 now abandoned, which is a continuation of application Ser. No. 423,373, filed Oct. 19, 1989, now abandoned which is a of application Ser. No. 279,430 filed Dec. 2, 1988, now U.S. Pat. No. 4,946,970.

BACKGROUND OF THE INVENTION

1. Field of the Invention

This invention relates to the control of dust that is emitted from aromatic anhydrides. More particularly, this invention relates to the suppression of dust emitted from solid aromatic anhydrides by treating the aromatic anhydride with an organic compound.

2. Prior Art

Aromatic anhydrides are useful industrial chemicals. Many of them are produced and used on the order of millions of pounds per year. For example, trimellitic anhydride (TMA) is used in the manufacture of vinyl plasticizers, which can be used in electrical wire insulation, refrigerator gasketing, automotive padding and upholstery, washable sheeting, and pool liners. TMA is used in water-soluble alkyd coatings. It is used in the production of high-temperature polymers, such as amide-imide polymers. TMA is used as a curing agent for epoxy resins. In addition, its derivatives are used in various specialty applications, such as dye intermediates, heavy duty detergents, agricultural chemicals, and pharmaceuticals. Aromatic dianhydrides in particular are useful for preparing high performance resin materials. However, aromatic anhydrides, particularly finely-divided aromatic anhydrides, are extremely difficult to handle because they emit relatively large amounts of dust. Dust from aromatic anhydrides can be irritating and TMA dust in particular can produce sensitization effects when inhaled.

Since much of the exposure to this dust occurs during the handling of the solid aromatic anhydrides, a suitable method for suppressing airborne aromatic anhydride dust particles is desired.

Various techniques have been used to suppress dust. For example, in U.S. Pat. No. 2,222,370, Mori disclosed a method for preventing and laying dust in coal mines by spraying the coal mine workings with a mixture or emulsion of petroleum oil and water, the water being present in an amount sufficient to make the oil spray noninflammable.

In U.S. Pat. No. 2,399,464, Butcher taught an improved liquid spraying agent adapted to inhibit the surface dusting of the soil in playgrounds, training camps, and dirt walks. The stable liquid dust-laying composition comprised a low-viscosity, low-volatility petroleum distillate oil, naphthenic acid, a wetting agent consisting essentially of a sodium salt of a sulfonated higher alcohol, water, and a germicide.

In U.S. Pat. No. 2,423,449, Heald, et al, disclosed treating soap to reduce dust-forming and lumping tendencies by spraying soap particles with a heavy mineral oil fraction.

In U.S. Pat. No. 2,585,026, Moen, et al, taught the reduction of dust produced by grain during handling by applying to the grain an emulsion of water and mineral oil.

In U.S. Pat. No. 3,913,637, Taylor taught the use of a liquid material such as white mineral oil to reduce the dust in a solid premix concentrate for addition to animal and poultry feed, the concentrate consisting essentially of gentian violet, a selective fungicidal mold inhibitor of "Candida albicaus," and inert ingredients.

In U.S. Pat. No. 4,276,308, Ito, et al, disclosed using a polybutene sticking agent in the preparation of granules containing a carboxylate, the granules being used safely as an effective wood preservative composition.

In Japanese Patent Publications Nos. 80037521, 50053538, and 56059701, there is taught a powdery agricultural agent giving less dusting, which powdery agricultural agent is prepared by mixing the active ingredient with a powdery inorganic carrier and polybutene or polyisobutene.

In U.S. Pat. No. 4,208,433, Darham, Jr., et al, disclosed the use of an oleaginous vehicle, such as corn oil, unrefined cottonseed oil, and soya oil, in the adsorption of dust into whole grain seeds to eliminate grain warehouse explosions, reduce fire hazards, and improve environmental conditions for humans.

In U.S. Pat. No. 4,490,511, Li, et al, disclosed a low-dusting anhydride curing agent blend for epoxy resins, which blend comprised a solid acid anhydride, TMA, and from 1 wt % to about 10 wt % normally liquid anhydride. The liquid anhydride was selected from methyl hexahydrophthalic anhydride, nadic methyl anhydride, and dodecyl succinic anhydride. The TMA flakes can be pre-wetted or the finely-divided TMA powder can be post-wetted with the liquid anhydride to provide the TMA with a greatly reduced dusting tendency.

There has now been found a method for suppressing dust emitted from solid aromatic anhydrides, which method employs the application of an organic compound to the aromatic anhydride that does not appreciably affect the aromatic anhydride in a deleterious manner and is selected from materials that are not liquid anhydrides.

SUMMARY OF THE INVENTION

There is provided a method for suppressing dust emitted from solid aromatic anhydrides, which method comprises treating said solid aromatic anhydrides with at least one organic compound wherein the organic compound is both liquid and substantially non-volatile at normal ambient temperatures and pressures and wherein the organic compound does not contain an anhydride functionality. Treating is carried out by spraying the solid aromatic anhydride, mixing the organic compound directly into the solid aromatic anhydride or applying a solution of the organic compound dissolved in a volatile solvent.

Also provided are stabilized aromatic anhydride compositions positions which emit reduced amounts of airborne dust. The compositions comprise a solid aromatic anhydride and an organic compound, the solid aromatic anhydride being present in an amount within the range of about 90 wt % to about 99.999 wt % and the organic compound being present in an amount within the range of about 0.001 wt % to about 10 wt %, each amount being based on the weight of the composition.

DESCRIPTION AND PREFERRED EMBODIMENTS

In view of the dusting tendency of solid aromatic anhydrides and the possible sensitization effect of TMA dust when inhaled, a suitable method for suppressing dust emitted from solid aromatic anhydrides is needed. A new method has been developed and this method is the subject of the present invention. The method for suppressing dust emitted from solid aromatic anhydrides comprises treating the aromatic anhydride with an organic compound wherein the organic compound is both liquid and substantially nonvolatile at normal ambient temperatures and pressures. Such organic compounds are characterized by their ability to reduce the amount of air-borne dust that is emitted from the aromatic anhydride and by their ability not to affect deleteriously the aromatic anhydride or products made with the aromatic anhydride.

The anhydrides that are of interest in this invention are the aromatic anhydrides that are solids at ordinary ambient temperatures and that have the following structure (I) as a portion of the anhydride molecule.

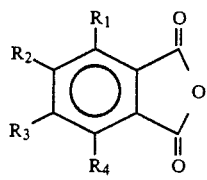

The groups $R_1$ through $R_4$ may be the same or they may be different and, without intending to limit the groups from which $R_1$ through $R_4$ may be selected, they may be hydrogen, alkyl, alkenyl, aromatic, alkylaromatic, fused ring aromatics to form, for example, a naphthalene nucleus, halogen, other anhydride or aromatic anhydride moieties, or sulfur, nitrogen or phosphorous containing moieties. Naphthalene dianhydride and naphthalene anhydride are examples of fused aromatic ring anhydrides. Preferably, the aromatic anhydrides have from eight to forty carbon atoms.

It is to be understood that the primary object of this invention is to provide aromatic anhydride compositions that have a reduced tendency to form deleterious dust. Another object of this invention is to provide a method for treating solid aromatic anhydrides with suitable organic compounds to suppress the formation of anhydride dust without deleteriously affecting the end use of the anhydride. The type of aromatic anhydride useful for this invention is not limited except that the anhydride is a solid at ordinary ambient temperatures and that it has as a portion of its molecular structure the structure (I) shown above.

Without limiting the scope of solid aromatic anhydrides suitable for the compositions and methods of this invention, the particularly preferred anhydrides are phthalic, anhydride, trimellitic anhydride, pyromellitic dianhydride, and 3,3',4,4'-biphenyltetracarboxylic dianhydride.

Anhydrides having the structure

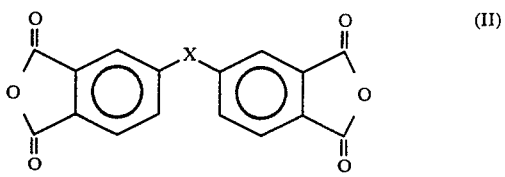

wherein x is

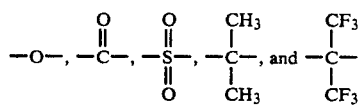

are also particularly preferred anhydrides. These are usually referred to, respectively, as oxybisphthalic anhydride, benzophenonetetracarboxylic dianhydride, sulfonylbisphthalic anhydride, isopropylidene bisphthalic anhydride and 2,2-bis(3,4-dicarboxyphenyl)hexafluoropropane dianhydride.

Particularly preferred anhydrides also include the category of anhydrides having the structure II above wherein X is selected from the group consisting of

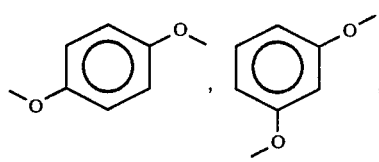

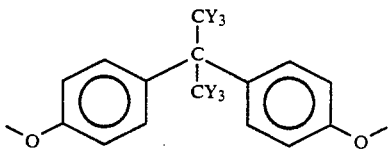

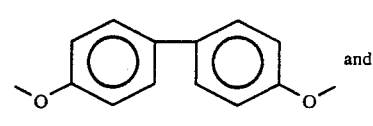

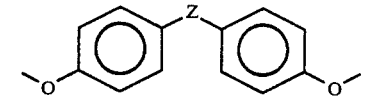

wherein Y is H or F and Z is

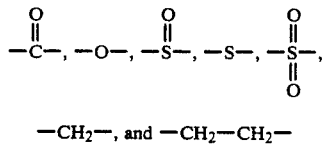

$-CH_2-$, and $-CH_2-CH_2-$

Trimellitic anhydride is one of the most preferred solid aromatic anhydride for the compositions and processes of this invention.

A general method for preparing aromatic anhydrides is the oxidation of the corresponding methyl substituted aromatic feedstock to the di- or poly-carboxylic acid. Carboxylic acid groups adjacent to one another on the aromatic ring may be dehydrated to an anhydride. Simple heating is usually sufficient to form the anhydride.

The methyl groups may be oxidized to carboxylic acids by any one of a number of methods known in the art as, for example, oxidation with potassium permanganate or air oxidation catalyzed by heavy metals.

Many of the anhydrides listed above as the particularly preferred anhydrides for this invention are commercially available. For example, phthalic anhydride and trimellitic anhydride are produced in quantities of millions of pounds per year. 3,3',4,4'-Biphenyltetracarboxylic acid dianhydride is also a commercial anhydride and it can be prepared, for example, by the oxidation of 3,3',4,4'-tetramethylbiphenyl to the tetracarboxylic acid by any one of a number of oxidizing agents such as potassium permanganate, and then heated to convert the tetracarboxylic acid into the anhydride by removing two molecules of water. Alternatively, phthalic acid can be coupled directly to prepare 3,3',4,4'-biphenyltetracarboxylic acid. The tetraacid can be dehydrated to the dianhydride. See for example U.S. Pat. No. 4,581,469. Pyromellitic dianhydride and the anhydrides having structure (II) wherein X is

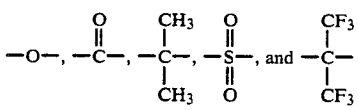

can be prepared by oxidizing the corresponding tetramethyl compound using any one of a number of methods for oxidizing the aromatic methyl groups to carboxylic acid groups, e.g. potassium permanganate oxidation or air oxidation catalyzed by heavy metals. The resulting tetracarboxylic acids are suitably dehydrated to produce the corresponding dianhydrides. U.S. Pat. Nos. 3,022,320 and 2,712,543 teach the preparation of sulfonylbisphthalic anhydride and isopropylidene bisphthalic anhydride, respectively, and G.B. Patent 1,019,573 teaches a method for preparing oxybisphthalic anhydride. The tetramethyl substituted feedstock for preparing 2,2-bis(3,4-dicarboxyphenyl)hexafluoropropane 2,2-bis(3,4-dicarboxyphenyl)hexafluoropropane dianhydride can be prepared by coupling o-xylene with hexafluoroacetone using an acid catalyst. Benzophenone tetracarboxylic dianhydride is commercially available from Aldrich Chemical Company, Milwaukee, Wis. The anhydrides having structure (II) wherein X is

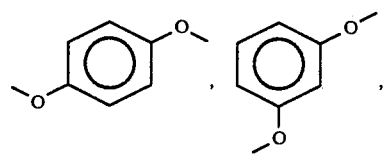

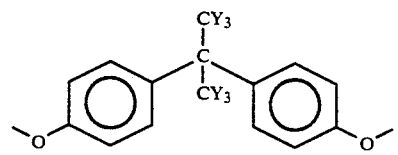

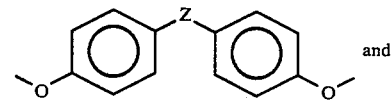
and

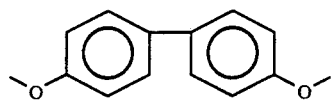

where Z and Y are as defined above, may be prepared, for example, by reacting the corresponding diphenol, such as hydroquinone, with two equivalents of 4-fluorophthalic anhydride in a nucleophillic aromatic substitution reaction. Such a process is taught in European Patent Application 0288974 and the references cited therein.

Suitable organic compounds useful for reducing the dust produced by solid aromatic anhydrides are those organic compounds that are both liquid and substantially non-volatile at normal ambient temperatures and pressures. Preferred compounds are hydrocarbons, esters, mineral oils, white oils, polybutenes or hydrogenated polybutenes, alcohols and poly-alpha-olefins. Particularly preferred compounds are white oil, polybutenes and hydrogenated polybutenes, 2-ethyl-hexanol, tri-octyl-trimellitate (TOTM), and tri-iso-nonyl-trimellitate.

The hydrocarbon materials suitable for reducing aromatic anhydride dust are those organic compounds comprising hydrogen and carbon atoms and may be linear, branched, saturated or unsaturated, aromatic or combinations of the above. It is preferred that these hydrocarbon compounds be liquid and substantially non-volatile at normal ambient temperatures and pressures. The preferred hydrocarbon have from six to one hundred carbon atoms and more preferably from eight to thirty carbon atoms.

A white oil is a highly refined lubricating oil fraction which has a colorless, water-white appearance. It is also odorless and tasteless and is essentially free of aromatic hydrocarbons, sulfur, and nitrogen. It has a color of +30 Saybolt and possesses a low absorbance of ultraviolet light. Typical white oils are prepared by means of a catalytic hydrogenation treatment of a lubricating oil fraction which has been dewaxed and/or solvent extracted and are used for cosmetics and certain medicinal purposes. A typical white oil for use as a dust-suppressing agent is a 55 white oil that can be obtained from Amoco Oil Company and is identified as Amoco White Mineral Oil No. 5-NF. Such white oil has a sulfur content that is less than 2 ppm (wt) and a nitrogen content that is less than 1 ppm (wt) and is approximately 50% paraffins and 50% naphthenes.

While white oil is a preferred compound of this invention for suppressing aromatic anhydride dust because it is odorless and colorless and does not impart undesirable characteristic to the treated aromatic anhydride, other refined oils both mineral and from animal and vegetable sources are also suitable dust suppressing agents of the invention. For example, vegetable oils selected from the group consisting of cotton seed, ground nut, soybean sunflower, rape, sesame, olive, corn, safflower, palm, palm kernel, coconut, linseed and castor oil are suitable vegetable oils. Suitable animal oils include beef tallow and lard oil. Suitable mineral oils are those refined oils from a petroleum source that have a viscosity in the range of about 1 cSt at 100° C. to about 100 cSt at 100° C.

Another suitable organic compound for suppressing aromatic anhydride dust comprises viscous polybutenes having a number average molecular weight in the range of about 250 to about 500 and a viscosity at 38° C. (100° F.) in the range of about 4 to about 1,100 centistokes. Such polybutenes are essentially water white, resistant to oxidation by light and heat, nondrying and thermally decompose without residue at a temperature above about 275° C. Such polybutenes may be obtained by the polymerization of a refinery butenes stream in the presence of a Friedel-Crafts-type catalyst. The refinery butenes stream, often identified as the "C$_4$" or "B-B" (Butanes-Butenes) olefin stream from petrochemical cracking units, is a convenient source of isobutylene, 1-butene, and cis- and trans-2-butene. The polybutenes comprise isobutylene-butene copolymers made up of high molecular weight mono-olefins (95 to 100%) and isoparaffins. Polybutenes suitable for use as a dust-suppressing agent are commercially available. Typical examples of suitable polybutenes are the Indopol L-4, Indopol L-10, Indopol L-14, Indopol L-50, and Indopol L-100 polybutenes provided by Amoco Chemical Company.

Moreover, hydrogenated polybutenes are suitable dust-suppressing agents for use with aromatic anhydrides. Hydrogenated polybutenes are available commercially. For example, they may be obtained from Amoco Chemical Company under the tradename Panalane. These hydrogenated polybutenes are prepared by hydrogenating, for example, the above-mentioned viscous polybutenes to hydrogenate all or most of the polybutene unsaturations.

The poly-alpha-olefin materials made by the dimerization, trimerization or oligomerization of alpha-olefins, such as $C_6$–$C_{20}$ alpha olefins, followed by a hydrogenation step to remove unsaturations are also suitable hydrocarbon organic compounds of this invention for suppressing aromatic anhydride dust. These materials are available in a variety of viscosities and molecular weights however they are all characterized by having excellent chemical inertness and excellent viscosity properties. They find wide use as synthetic lubricants. They are liquid and substantially non-volatile at normal ambient conditions. They are available from, for example, Gulf Chemical Company. The poly-alpha-olefins made from the dimerization and trimerization of a $C_{10}$-alpha olefin is a particularly suitable poly-alpha-olefin compound suitable for suppressing dust from aromatic anhydrides.

Alcohols and mixtures of alcohols are also organic compounds useful for suppressing aromatic anhydride dust formation. In order to be effective the alcohol should be both substantially non-volatile and liquid at normal ambient temperatures and pressures. A liquid alcohol is easier to apply to the aromatic anhydride and also may provide a coating action to control dust formation. Suitable alcohols are the mono-hydroxylic alcohols that have six or more carbon atoms and preferably six to 30 carbon atoms. They may be linear, branched, cyclic, heterocyclic or aromatic. Examples of alcohols in this category, without intending to limit the alcohols useful for this invention, include the hexanols, e.g., 1-hexanol, 2-hexanol, cyclohexanol; the heptanols, the octanols, e.g. 2-ethylhexanol, iso-octanol and 1-octanol, and iso-nonyl alcohol. Diols such as ethylene glycol or propylene glycol are also suitable alcohols. These diols are liquid and substantially non-volatile at normal ambient temperatures and pressures. Other diols with three or more carbon atoms and preferably three to thirty carbon atoms are also suitable. Alcohols with three or more hydroxyl groups are also suitable alcohols, i.e. glycerol and the so called polyols. These polyhydroxy compounds preferably have from three to six hydroxy groups and three to thirty carbon atoms. A particularly preferred alcohol is 2-ethylhexanol since 2-ethylhexanol is widely used for preparing esters of trimellitic anhydride or acid. It can be obtained commercially from Eastman Chemicals, Ashland Chemical, Shell Chemical and Union Carbide. Nonyl alcohol, also called iso-nonyl alcohol is also particularly preferred. It can be obtained from Exxon Chemical Company.

Esters and mixtures of esters are also organic compounds useful for reducing dust from aromatic anhydrides. The esters that are useful are those that are liquid and substantially non-volatile at normal ambient temperatures and pressures. Particularly suitably esters are those esters made from aromatic mono-, di- and polycarboxylic acids. Esters made from aliphatic carboxylic acids are also useful. These acids may be mono-, di- or poly-carboxylic. They may be linear, branched, cyclic, saturated or unsaturated. Adipic and oleic acid are examples of these acids. Preferably these acids have from one to thirty carbon atoms.

The particularly preferred esters useful for suppressing aromatic anhydride dust are the esters of acids selected from the group consisting of terephthalic acid, isophthalic acid, phthalic acid, trimellitic acid, pyromellitic acid, a naphthalene carboxylic acid, a naphthalene dicarboxylic acid, oleic acid and adipic acid.

The esters of the solid, dust forming aromatic anhydrides are also suitable organic compounds for suppressing anhydride dust. For example, a suitable dust suppressant for benzophenonetetracarboxylic dianhydride is the ester of benzophenonetetracarboxylic acid. Thus, the esters of the acids formed by hydrolyzing the above-mentioned particularly preferred aromatic anhydrides are suitable organic compounds for suppressing aromatic anhydride dust.

The ester organic compounds of this invention are prepared by esterifying the acid components with an alcohol. The alcohol may be any alcohol. Suitable alcohols, without intending to limit the choice of alcohol, are for example, methanol, ethanol, propanols, butanols, 2-ethylhexanol, isooctanol, glycols or polyols or mixtures of these or other alcohols. The alcohols can be linear, branched, cyclic or aromatic. The preferred alcohols, glycols and polyols used for preparing these esters contain from one to thirty carbon atoms. Particularly preferred alcohols are 2-ethylhexanol and iso-nonyl alcohol.

Tri-octyl-trimellitate (TOTM), prepared by esterifying trimellitic acid or trimellitic anhydride with 2-ethylhexanol is a particularly preferred ester for reducing aromatic anhydride dust formation. Tri-iso-nonyl trimellitate, prepared by esterifying trimellitic anhydride with iso-nonyl alcohol is also a particularly preferred ester for reducing aromatic anhydride dust formation.

For the purposes of this invention normal ambient temperatures and pressures means those normally experienced atmospheric conditions that exist outdoors or indoors such as in a chemical or manufacturing plant environment. In a preferred embodiment of this invention, the organic compound should be a liquid when it is applied to the aromatic anhydride and should remain liquid. This facilitates application and dust-suppression, respectively. However, it is not an absolute requirement that the organic compound contemplated by this invention be liquid at ambient temperature and pressure.

They may also be solid and can be heated or dissolved in a solvent to facilitate application to the aromatic anhydride. The organic compounds of this invention useful for suppressing aromatic anhydride dust may be liquids in only part of the temperature and pressure range of normal ambient temperatures and pressures.

In one embodiment, the organic compound selected as a dust suppressant for the aromatic anhydride is a compound that is liquid at normal ambient temperatures and pressures but it is volatile at a selected temperature used for the processing of the anhydride in some later manufacturing process. In this embodiment, the organic compound will serve to function as a dust suppressant during the handling of the aromatic anhydride; however, the dust suppressant will be substantially or totally removed during the manufacturing step incorporating the aromatic anhydride into a product. Thus, where a dianhydride, for example, is used to make a polyimide, a dust suppressant can be selected that is non-volatile at normal ambient temperatures and pressures, but is volatile at the temperature used to condense the dianhydride with the amine to make the polyimide thereby removing the dust suppressant from the final product.

Pursuant to the method of the present invention, the aromatic anhydride is contacted with the organic compound in order to coat the surface of the aromatic anhydride with the organic compound. Generally, the solid aromatic anhydride is present in the form of powder, flakes, crystals, briquettes, pellets, or pastilles.

The organic compound can be applied to the aromatic anhydride in at least one of three ways. Preferably, the aromatic anhydride is contacted with the organic compound by spraying the organic compound on the surface of the aromatic anhydride. Alternatively, agitation can be used and the organic compound is stirred directly into the solid aromatic anhydride material. Thirdly, a diluent is added to the organic compound in order to achieve a more uniform application of the compound. The organic compound and diluent combination is applied either by spraying or by direct stirring. The diluent is removed subsequently. A suitable diluent may be any volatile solvent that is miscible with the organic compound.

The treating should be such as to put on the surface of the aromatic anhydride an amount of organic compound that is within the range of about 10 ppm by weight (0.001 wt %) to about 100,000 ppm by weight (10 wt %); suitably, within the range of about 50 ppm by weight (0.005 wt %) to about 20,000 ppm by weight (2 wt %); and, preferably, within the range of about 100 ppm by weight (0.01 wt %) to about 2,000 ppm by weight (0.2 wt %), based on the weight of the treated aromatic anhydride.

According to the present invention, there is also provided stabilized aromatic anhydride compositions having a reduced tendency to form dust, which compositions comprise the solid aromatic anhydride treated with at least one organic compound wherein the organic compound is both liquid and substantially non-volatile at normal ambient temperatures and pressures and the solid aromatic anhydride being present in an amount within the range of about 90 wt % to about 99.999 wt %, based on the total weight of the composition, and the organic compound being present in an amount within the range of about 0.001 wt % to about 10 wt %, based on the total weight of the composition. These compositions are prepared conveniently by the method of the present invention.

The following examples are presented to facilitate a better understanding of the methods and compositions of the present invention and to illustrate the present invention and are not intended to limit the scope of the present invention.

EXAMPLE I

A qualitative test was performed to show the effectiveness of the method of the present invention.

An untreated sample of TMA flakes, Sample No. 1, was tumbled for 1 hr at 90–120 rpm in a stainless steel mixing jar equipped with inner baffles. The tumbled TMA was collected and placed in a transparent glass jar suitable for viewing clearly the contents of the jar.

To a second sample of TMA, Sample No. 2, were added 500 ppm of the white oil. Sample No. 2 was then tumbled under the same conditions as Sample No. 1. Visual comparison between the two TMA samples was made in regard to the amount of airborne TMA dust generated when the samples were shaken and opened in a fume hood. Dust was observed exiting the untreated sample, Sample No. 1. On the other hand, the treated TMA sample, Sample No. 2, had comparatively very little TMA dust emanating from the jar.

EXAMPLE II

Several tests were conducted to determine the amount of airborne TMA dust that would result when a selected TMA sample was subjected to agitation. The test system was made up of an agitation source for shaking the TMA sample and a collection device for collecting airborne TMA dust. The agitation source was a sieve shaker and was employed to cause dust to become airborne when the TMA sample was shaken. Once airborne, the TMA dust was collected in the collection device, which consisted of a small portable vacuum pump connected to a Millipore matched weight aerosol filter cassette. The matched weight filter cassette consisted of a set of two filters of equal weight in series. Filters of the same filter cassette were manufactured to weigh within ±0.0001 gm of each other. The TMA dust was collected on the first filter and the difference in weight between the first and second filters was equivalent to the amount of TMA dust that was collected on the first filter.

Each test was conducted in the following manner. The TMA sample (100 gm) was placed in a 16-oz jar having an 89 mm cap. The jar was agitated by the sieve shaker and the airborne TMA dust was sampled for 1 hr. The setting for the vacuum pump was 1.2 liters/min. All weighings were performed on a laboratory analytical balance. Samples Nos. 3, 4, and 5 were run as blanks (air samples), i.e., there was no TMA in the sample jar. Samples Nos. 6 and 7 were untreated TMA. Samples Nos. 8 and 9 were TMA treated with 1,000 ppm white oil while Samples Nos. 10 and 11 were TMA treated with 1,000 ppm trioctyltrimellitate (TOTM).

The results of these tests are presented hereinbelow in Table I.

TABLE I

| | TMA Dust Suppression | | |
|---|---|---|---|
| | | Weight, gm | |
| Sample No. | Sample Description | 1st Filter | 2nd Filter | Delta Weight |
| 3 | air | 0.0443 | 0.0443 | 0.0000 |
| 4 | air | 0.0452 | 0.0451 | 0.0001 |
| 5 | air | 0.0450 | 0.0450 | 0.0000 |

TABLE I-continued

| | | TMA Dust Suppression | | |
|---|---|---|---|---|
| | | | Weight, gm | |
| Sample No. | Sample Description | 1st Filter | 2nd Filter | Delta Weight |
| 6 | TMA | 0.0486 | 0.0450 | 0.0036 |
| 7 | TMA | 0.0475 | 0.0450 | 0.0025 |
| 8 | TMA + white oil (1,000 ppm) | 0.0519 | 0.0512 | 0.0007 |
| 9 | TMA + white oil (1,000 ppm) | 0.0488 | 0.0487 | 0.0001 |
| 10 | TMA + TOTM (1,000 ppm) | 0.0515 | 0.0509 | 0.0006 |
| 11 | TMA + TOTM (1,000 ppm) | 0.0447 | 0.0452 | −0.0005 |

The tests made with air samples, i.e., Samples Nos. 3, 4, and 5, demonstrated that no weight gain occurred when air was the sample. This suggested that the environmental dust was negligible under the test application and only TMA dust was being collected when TMA samples were subjected to the test. Both the white oil and TOTM reduced or suppressed the dust of the TMA.

EXAMPLE III

A series of tests was conducted to confirm the results of the tests performed in Example I and minimize the effects of experimental and instrumental error. In these tests, 125-gm samples were used, the sampling time was extended to 5 hr, and the vacuum setting was maintained at 2.8 l/min. In addition, the amounts of the material added to suppress the dust were varied. The test system was the same as that employed in the tests conducted in Example II.

The results of these tests are presented hereinbelow in Table II.

TABLE II

| | TMA Dust Suppression[1] | | | | |
|---|---|---|---|---|---|
| Sample No. | Treatment | | Weight, gm | | |
| | Agent | Amount, ppm | 1st Filter | 2nd Filter | TMA Dust |
| 12 | — | — | 0.1595 | 0.0445 | 0.1150 |
| 13 | TOTM | 100 | 0.0518 | 0.0438 | 0.0080 |
| 14 | TOTM | 250 | 0.0568 | 0.0452 | 0.0116 |
| 15 | TOTM | 500 | 0.0546 | 0.0457 | 0.0089 |
| 16 | TOTM | 750 | 0.0464 | 0.0447 | 0.0017 |
| 17 | TOTM | 1,000 | 0.0488 | 0.0447 | 0.0041 |
| 18 | — | — | 0.0846 | 0.0445 | 0.0401 |
| 19 | OIL[2] | 100 | 0.0464 | 0.0443 | 0.0021 |
| 20 | OIL[2] | 250 | 0.0456 | 0.0449 | 0.0007 |
| 21 | OIL[2] | 750 | 0.0488 | 0.0482 | 0.0006 |
| 22 | OIL[2] | 1,000 | 0.0461 | 0.0457 | 0.0004 |
| 23 | P[3] | 1,000 | 0.0458 | 0.0451 | 0.0007 |

[1]For 125-gm sample at vacuum setting of 2.8 l/min and setting time of 5 hr
[2]OIL is white oil
[3]P is Panalane (hydrogenated polybutenes)

These data suggest that as the amount of dust-suppressing agent is increased, the amount of detected dust is decreased. In addition, the data indicate that white oil has better dust-suppressing ability than TOTM.

EXAMPLE IV

These tests were conducted in order to ascertain whether the method for dust suppression of the present invention would interfere with TMA end-use applications. Untreated TMA and TMA treated with either white oil or TOTM were esterified with 2-ethylhexanol. Color evaluations of each of the esterification products were made by measuring the color of the crude and final ester using the APHA color scale. The color of the TMA was measured via a spectrophotomeric method identified as the ΔE method for TMA, wherein the total color difference between a solution of 3N NaOH and a solution composed of 5 gm of TMA dissolved in 30 ml of 3N NaOH was obtained. The ΔE value is related to the color of the TMA product in the 400 to 700 nm wavelength range as measured by a spectrophotometer.

The results of these color measurements are presented hereinbelow in Table III.

TABLE III

| | TMA Dust Suppression Applications | | | | |
|---|---|---|---|---|---|
| Sample No. | Treatment | Cook time, hr | ΔE | FEC[1] | CEC[2] |
| 24 | — | 5 | 2.43 | 30 | 45 |
| 25 | 0.1 wt % oil[3] | 4 | — | 30 | 45 |
| 26 | 0.1 wt % TOTM | 4.75 | — | 30 | 45 |

[1]FEC is final ester color
[2]CEC is crude ester color
[3]Oil is white oil

These data indicate that neither the white oil nor the TOTM caused color problems in esterifications of TMA with 2-ethylhexanol. The sample treated with white oil and the sample treated with TOTM gave no observable difference in the crude ester color or final ester color of TOTM, when compared to the untreated TMA sample. Crude ester color is the color of the crude esterification reaction mixture. Final ester color is the color of the ester after treatment with 1% activated carbon and an alcohol stripping procedure to remove excess alcohol used during the esterification.

EXAMPLE V

Additional tests were conducted to determine whether the dust-suppressing agent would be detrimental to the TMA end-use applications. These tests were conducted according to the procedure described hereinabove in Example IV, with the exception that 10,000 ppm of white oil or 10,000 ppm (wt) of TOTM were employed.

The results of the color measurements are presented hereinbelow in Table IV.

TABLE IV

| | TMA Dust Suppression Applications | | | | |
|---|---|---|---|---|---|
| Sample No. | Treatment | Cook time, hr | ΔE | FEC[1] | CEC[2] |
| 27 | — | 4.5 | 3.03 | 35 | 40 |
| 28 | 0.1 wt % oil[3] | 4.5 | 3.02 | 30 | 45 |
| 26 | 0.1 wt % TOTM | 4.0 | 3.08 | 35 | 45 |

[1]FEC is final ester color
[2]CEC is crude ester color
[3]Oil is white oil

Again, neither the white oil nor the TOTM caused color problems in esterifications of TMA with 2-ethylhexanol.

EXAMPLE VI

The trimellitate esters described in Table III were used as plasticizers for preparing clear polyvinyl chloride (PVC) sheets. The sheets were evaluated in a variety of testing procedures to determine if the 0.1 percent TOTM or 0.1 percent white oil added to the TMA would cause performance deficiencies in end use products.

The performance test data given in Table V demonstrate that these materials do not cause performance deficiencies in PVC sheets. The performance test data are equivalent for the treated and untreated TMA. The performance tests include: Tensile Properties, Activated Carbon Volatility, Soapy Water Extraction, Mineral Oil Extraction, Humidity Compatibility, Roll Spew-Exudation, Shore A Hardness and Brittleness Temperature.

TABLE V

Performance Evaluation of Clear Polyvinyl Chloride Sheets Formulated with TOTM Plasticizer Made From TMA Treated With White Oil or TOTM

| | TMA Treatment (TOTM Sample No.) | | |
|---|---|---|---|
| | None (24) | 0.1% Oil (25) | 0.1% TOTM (26) |
| Tensile Properties | | | |
| Tensile Strength (PSI) | 3387 | 3321 | 3319 |
| 100% Modulus (PSI) | 2255 | 2322 | 2235 |
| 300% Modulus (PSI) | 3194 | 3180 | 3039 |
| % Elongation | 349 | 351 | 347 |
| Activated Carbon Volatility - Percent Weight Loss (90° C.) | | | |
| 24 hours | 0.5 | 0.5 | 0.5 |
| 48 hours | 0.6 | 0.6 | 0.6 |
| Soapy Water Extraction - Percent Weight Loss (90° C.) | | | |
| 48 Hours | 0.2 | 0.2 | 0.2 |
| 72 Hours | 0.2 | 0.2 | 0.2 |
| Mineral Oil Extraction - Percent Weight Loss (70° C.) | | | |
| 24 hours | 2.4 | 2.3 | 2.3 |
| Humidity Capatibility - Exudation (90° C.) | | | |
| 7 days | None | None | None |
| Roll Spew - Exudation (Room Temperature) | | | |
| 96 hours | None | None | None |
| Shore A Hardness | | | |
| Initial | 94 | 94 | 93 |
| 10 seconds | 89 | 89 | 88 |
| Brittleness Temperature | | | |
| Degrees C. | −22 | −24.9 | −22.8 |

EXAMPLE VII

The trimellitate esters described in Table III were used to formulate UL 105° C. polyvinyl chloride electrical wire insulation materials. These PVC materials were evaluated in a variety of testing procedures to determine if the 0.1 percent TOTM or 0.1 percent white oil added to the TMA would result in performance problems in end use products.

The performance test data, given in Table VI, show that these materials do not cause performance problems in PVC wire insulation formulated with plasticizer made with treated TMA. The performance tests include: Initial tensile strength measurements, tensile strength measurements after seven days at 136° C., and the percent retention of tensile strength after the seven-day treatment.

TABLE VI

Performance Evaluation of Wire Insulation Formulated With TOTM Plasticizer Made From TMA Treated With White Oil or TOTM Dust Suppressant

| | TMA Treatment (TOTM Sample No.) | | |
|---|---|---|---|
| | None (24) | 0.1% Oil (25) | 0.1%.TOTM (26) |
| Tensile Properties | | | |
| Tensile Strength (PSI) | 3424 | 3404 | 3319 |
| 100% Modulus (PSI) | 2358 | 2325 | 2342 |
| 300% Modulus (PSI) | 3109 | 3099 | 3000 |
| % Elongation | 363 | 363 | 353 |
| Aged 7 Days at 136° C. | | | |
| Tensile Strength (PSI) | 3596 | 3544 | 3461 |
| 100% Modulus (PSI) | 2683 | 2784 | 2712 |
| 300% Modulus (PSI) | 3315 | 3439 | 3336 |

TABLE VI-continued

Performance Evaluation of Wire Insulation Formulated With TOTM Plasticizer Made From TMA Treated With White Oil or TOTM Dust Suppressant

| | TMA Treatment (TOTM Sample No.) | | |
|---|---|---|---|
| | None (24) | 0.1% Oil (25) | 0.1%.TOTM (26) |
| % Elongation (PSI) | 348 | 330 | 321 |
| Percent Retention | | | |
| Tensile Strength | 105 | 104 | 104 |
| 100% Modulus | 114 | 119 | 116 |
| 300% Modulus | 107 | 111 | 111 |
| % Elongation | 96 | 91 | 91 |

EXAMPLE VIII

The trimellitate esters decribed in Table IV were used as plasticizers to prepare clear polyvinyl chloride (PVC) sheets. These sheets were evaluated in a variety of testing procedures to determine if the 1.0 percent TOTM or 1.0 percent white oil added to the TMA would cause performance problems in an end use product. A treatment with 1 percent (10,000 PPM) TOTM or white oil represents a relatively high treat rate and if performance problems are to occur, they would be most apparent at these higher treat rates.

The performance data in Table VII demonstrate that the polyvinyl chloride sheets formulated with plasticizer made from TMA treated with 1 percent TOTM or 1 percent white oil are essentially equivalent to the base case where no TOTM or white oil was added to the TMA used to make the plasticizer.

TABLE VII

Performance Evaluation of Clear Polyvinyl Chloride Sheets Formulated with TOTM Plasticizer Made From TMA Treated With White Oil or TOTM Dust Suppressant

| | TMA Treatment (TOTM Sample No.) | | |
|---|---|---|---|
| | None (27) | 0.1% Oil (28) | 0.1% TOTM (29) |
| Tensile Properties | | | |
| Tensile Strength (PSI) | 3437 | 3551 | 3425 |
| 100% Modulus (PSI) | 22.51 | 2398 | 2275 |
| 300% Modulus (PSI) | 3078 | 3209 | 3057 |
| % Elongation | 375 | 365 | 375 |
| Activated Carbon Volatility - Percent Weight Loss (90° C.) | | | |
| 24 hours | 0.6 | 0.7 | 0.5 |
| 48 hours | 0.6 | 0.9 | 0.6 |
| Soapy Water Extraction - Percent Weight Loss (90° C.) | | | |
| 48 Hours | 0.2 | 0.5 | 0.2 |
| 72 Hours | 0.3 | 0.5 | 0.3 |
| Mineral Oil Extraction - Percent Weight Loss (70° C.) | | | |
| 24 hours | 2.5 | 2.1 | 2.5 |
| Humidity Capatibility - Exudation (90° C.) | | | |
| 7 days | None | None | None |
| Roll Spew - Exudation (Room Temperature) | | | |
| 96 hours | None | None | None |
| Shore A Hardness | | | |
| Initial | 95 | 95 | 95 |
| 10 seconds | 91 | 91 | 92 |
| Brittleness Temperature | | | |
| Degrees C. | −24.2 | −22.8 | −23.6 |

EXAMPLE IX

The trimellitate esters described in Table IV were used to formulate UL 105° C. polyvinyl chloride electrical wire insulation materials. These PVC materials were evaluated in a variety of testing procedures to determine if the 1.0 percent TOTM or 1.0 percent white oil added to the TMA would result in performance deficiencies in the end use product. A treatment with 1 percent (10,000 PPM) TOTM or white oil represents a relatively high treat rate and if performance problems are to occur, they would be most apparent at these higher treat rates.

The performance data in Table VIII demonstrate that the polyvinyl chloride wire insulation materials formulated with plasticizer made from TMA treated with 1 percent TOTM or 1 percent white oil are essentially equivalent to the base case material that was formulated with TOTM made from untreated TMA.

TABLE VIII

Performance Evaluation of Wire Insulation Formulated With TOTM Plasticizer Made From TMA Treated With White Oil or TOTM Dust Suppressant

| | TMA Treatment (TOTM Sample No.) | | |
|---|---|---|---|
| | None (27) | 0.1% Oil (28) | 0.1%.TOTM (29) |
| Tensile Properties | | | |
| Tensile Strength (PSI) | 3404 | 3668 | 3412 |
| 100% Modulus (PSI) | 2408 | 2595 | 2401 |
| 300% Modulus (PSI) | 3263 | 3392 | 3231 |
| % Elongation | 345 | 347 | 354 |
| Aged 7 Days at 136° C. | | | |
| Tensile Strength (PSI) | 3668 | 3777 | 3635 |
| 100% Modulus (PSI) | 2859 | 2973 | 2849 |
| 300% Modulus (PSI) | 3436 | 3517 | 3471 |
| % Elongation (PSI) | 340 | 335 | 333 |
| Percent Retention | | | |
| Tensile Strength | 107 | 103 | 106 |
| 100% Modulus | 119 | 115 | 118 |
| 300% Modulus | 106 | 104 | 107 |
| % Elongation | 98 | 96 | 94 |

EXAMPLE X

TMA treated with 0.1 percent (1000 PPM) TOTM and 0.1 percent white oil were also used to prepare water-borne alkyd and polyester resins that are used as coatings. There were no observable defects in appearance of the applied films, e.g., "fish eyes," craters or loss-of-gloss, and there were no differences in the physical performance properties of the coatings prepared with the treated TMA compared to coatings made with untreated TMA. These evaluations prove that the TMA treated with the organic compounds of this invention is acceptable for preparing water-borne coatings, a major end use for TMA.

EXAMPLE XI

Using the procedure described in Example II, 125 grams of untreated phthalic anhydride flakes were placed in a capped 16 oz. jar and agitated by the sieve shaker. The jar was sampled for 5 hours with the vacuum setting maintained at 4 liters/minute. During these 5 hours, 80.6 mg of phthalic anhydride dust were collected. In a repeat of this test using 125 grams of phthalic anhydride treated with 1000 parts per million of white oil, 0.6 mg of phthalic anhydride dust was collected on the filters during the 5 hour period. These data show that the application of the white oil resulted in a large reduction in the amount of airborne phthalic anhydride dust produced.

EXAMPLE XII

Following the procedure of Example XI, 125 grams of untreated pyromellitic dianhydride crystals were agitated for 5 hours. During this time 44.2 mg of pyromellitic dianhydride dust were collected on the filter. In a repeat of this test using 125 grams of pyromellitic dianhydride treated with 1000 parts per million of white oil only 1.0 mg of airborne pyromellitic dianhydride dust was collected on the filter. These data show that the application of the white oil dust suppressant resulted in a large reduction in the amount of airborne pyromellitic anhydride dust produced.

What is claimed is:

1. An aromatic anhydride composition having a reduced tendency to form dust comprising a solid aromatic anhydride treated with an organic compound, said organic compound being applied to the surface of said solid aromatic anhydride, wherein the solid aromatic anhydride is solid at normal ambient temperatures and is selected from the group consisting of trimellitic anhydride, phthalic anhydride, pyromellitic dianhydride, 3,3',4,4'-biphenyltetracarboxylic dianhydride and aromatic anhydrides having structure:

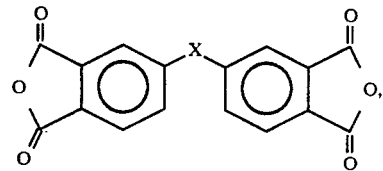

wherein X is:

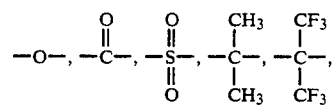

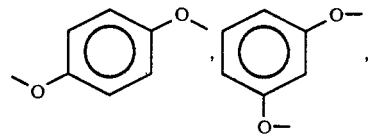

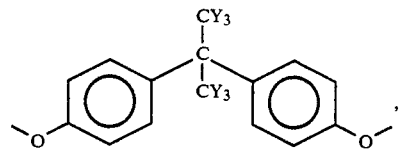

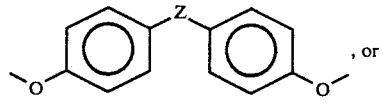

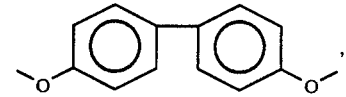

and Y is H or F and Z is:

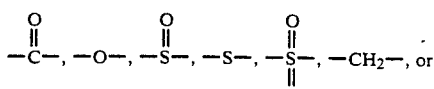

and the organic compound in both liquid and substantially non-volatile at normal ambient temperatures and pressures, does not contain an anhydride functionality and is selected from the group consisting of hydrocarbons that are linear, branched, saturated or unsaturated, aromatic or combinations thereof, white oils, refined mineral oils, refined vegetable oils, refined animal oils, viscous polybutenes having a number average molecular weight in the range of about 250 to about 500 and a viscosity at 38° C. (100° F.) in the range of about 4 to about 1,100 centistrokes, hydrogenated polybutenes, poly-alpha-olefin materials made by the dimerization, trimerization or oligomerization of C6-C20 alpha-olefins followed by hydrogenation, mono-hydroxylic alcohols having six to thirty carbon atoms, ethylene glycol and diols having three to thirty carbon atoms, polyhydroxy alcohols having three to six hydroxy groups and from three to thirty carbon atoms, and esters made from aromatic mono-, di- and polycarboxylic acids and aliphatic mono-, di- and polycarboxylic acids, and said acids having from one to thirty carbon atoms; the aromatic anhydride being present in an amount within the range of about 90 wt. % to about 99.999 wt. %, based on the total weight of the composition, and the organic compound being present in an amount within the range of about 0.001 wt. % to about 10 wt. % based on the total weight of the composition.

2. A method for suppressing dust emitted from an aromatic anhydride that is solid at normal ambient temperature which method comprises treating the aromatic anhydride with at least one organic compound, wherein the organic compound is both liquid and substantially non-volatile at normal ambient temperatures and pressure, wherein the organic compound does not contain an anhydride functionality, and wherein the organic compound is applied to the surface of the aromatic anhydride, said aromatic compound being selected from the group consisting of:

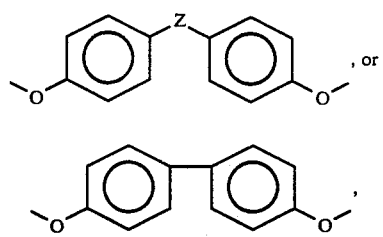

wherein X is:

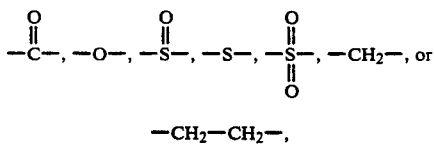

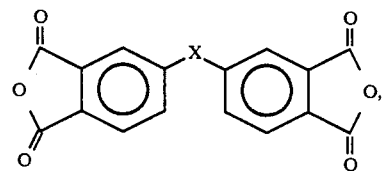

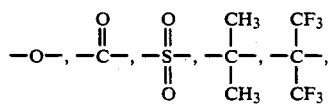

, or

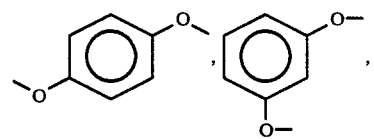

, and Y is H or F and Z is:

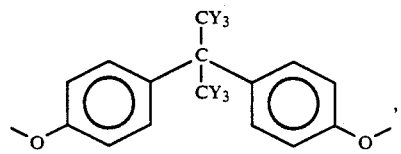

$-CH_2-CH_2-$, and said organic compound being selected from the group consisting of hydrocarbons that are linear, branched, saturated or unsaturated, aromatic or combinations thereof, white oils, refined mineral oils, refined vegetable oils, refined animal oils, viscous polybutenes having a number average molecular weight in the range of about 250 to about 500 and a viscosity at 38° C. (100° F.) in the range of about 4 to about 1,100 centistrokes, hydrogenated polybutenes, poly-alpha-olefin materials made by the dimerization, trimerization or oligomerization of C6-C20 alpha-olefins followed by hydrogenation, mono-hydroxylic alcohols having six to thirty carbon atoms, ethylene glycol and diols having three to thirty carbon atoms, polyhydroxy alcohols having three to six hydroxy groups and from three to thirty carbon atoms, and esters made from aromatic mono-, di- and poly-carboxylic acids and aliphatic mono-, di- and polycarboxylic acids, and said acids having from one to thirty carbon atoms.

3. The method of claim 2 wherein said treating comprises contacting the aromatic anhydride with the organic compound, the organic compound being stirred directly into the aromatic anhydride by means of agitation.

4. The method of claim 2 wherein said treating comprises spraying the aromatic anhydride with the organic compound.

5. The method of claim 2 wherein said treating comprises applying the organic compound to the aromatic anhydride as a solution of the organic compound in a volatile solvent.

6. The method of claim 2 wherein the aromatic anhydride is treated with the organic compound to provide on the aromatic anhydride an amount of organic compound that is within the range of about 10 ppm (by weight) to about 100,000 ppm (by weight), based on the weight of treated aromatic anhydride.

7. The method of claim 2 wherein the aromatic anhydride is treated with the organic compound to provide on the aromatic anhydride an amount of organic compound that is within the range of about 100 ppm (by weight) to about 2000 ppm (by weight), based on the weight of treated aromatic anhydride.

8. The method of claim 2 wherein the organic compound is an ester of an acid selected from the group consisting of terephthalic acid, isophthalic acid, trimellitic acid, phthalic acid, adipic acid and oleic acid.

9. The method of claim 2 wherein the organic compound is an ester of an acid selected from the group consisting of isophthalic acid, terephthalic acid, trimellitic acid, phthalic acid, pyromellitic acid, 3,3',4,4'-biphenyltetracarboxylic acid and aromatic acids having the structure

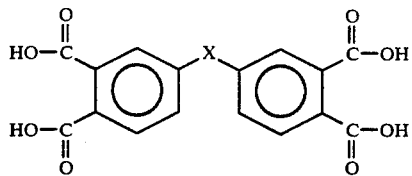

wherein X is selected from

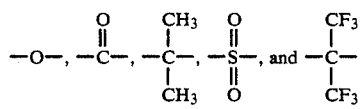

10. The method of claim 2 wherein the organic compound is an ester of an acid selected from the group consisting of isophthalic acid, terephthalic acid, trimellitic acid, phthalic acid, pyromellitic acid, and acids having the structure

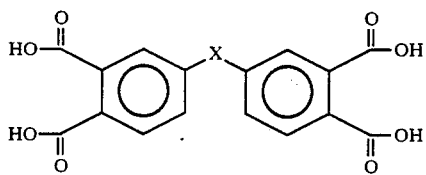

wherein X is selected from the group consisting of

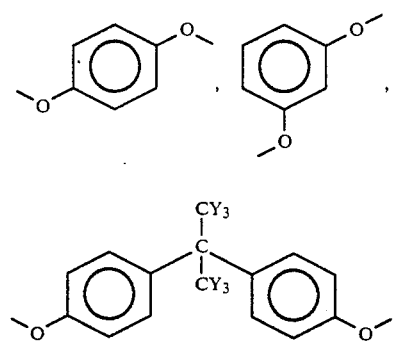

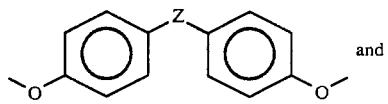

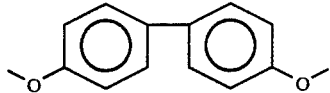

wherein Y is H or F and Z is selected from

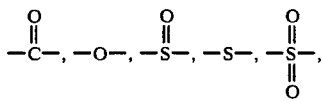

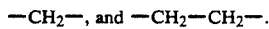

11. The method of claim 2 wherein the aromatic anhydride is trimellitic anhydride and the organic compound is iso-nonyl alcohol.

12. The method of claim 2 wherein the aromatic anhydride is trimellitic anhydride and the organic compound is tri-iso-nonyl trimellitate.

13. The composition of claim 1 wherein the aromatic anhydride is trimellitic anhydride and the organic compound is tri-iso-nonyl trimellitate.

14. The composition of claim 1 wherein the aromatic anhydride is trimellitic anhydride and the organic compound is iso-nonyl alcohol.

15. The composition of claim 1 wherein the solid aromatic anhydride is pyromellitic dianhydride.

16. The method of claim 2 wherein the aromatic anhydride is pyromellitic dianhydride.

17. The composition of claim 1 wherein the aromatic anhydride is present within the range of about 98 wt. % to about 99.995 wt. %, based on the weight of the composition, and the organic compound being present in an amount within the range of about 0.005 wt. % to about 2 wt. %, based on the weight of the composition.

18. The composition of claim 1 wherein the aromatic anhydride is present within the range of about 99.8 wt. % to about 99.99 wt. %, based on the weight of the composition, and the organic compound being present in an amount within the range of about 0.01 wt. % to about 0.2 wt. %, based on the weight of the composition.

* * * * *

UNITED STATES PATENT AND TRADEMARK OFFICE
CERTIFICATE OF CORRECTION

PATENT NO.: 5,235,070
DATED: 10 August 1993
INVENTOR(S): Michael R. Green, et al.

It is certified that error appears in the above-identified patent and that said Letters Patent is hereby corrected as shown below:

| Col. | Line | |
|---|---|---|
| 1 | 8-9 | "which is a of application" should read --which is a CIP of application--. |
| 14 | 44 | in Table VII, under the column "None (27)" and in the line "100% Modulus (PSI)," patent reads "22.51" should read --2251--. |

Signed and Sealed this

Seventh Day of June, 1994

Attest:

BRUCE LEHMAN

Attesting Officer    Commissioner of Patents and Trademarks